(12) United States Patent
Gross et al.

(10) Patent No.: US 8,933,994 B2
(45) Date of Patent: Jan. 13, 2015

(54) SYSTEMS AND METHODS FOR SPECIFYING AND FORMULATING CUSTOMIZED TOPICAL AGENTS

(71) Applicant: Skin Republic, Inc., Palo Alto, CA (US)

(72) Inventors: David B. Gross, Menlo Park, CA (US); Leslie Y. Harvill, El Granada, AA (US)

(73) Assignee: Skin Republic, Inc., Palo Alto, CA (US)

( * ) Notice: Subject to any disclaimer, the term of this patent is extended or adjusted under 35 U.S.C. 154(b) by 0 days.

(21) Appl. No.: 14/213,160

(22) Filed: Mar. 14, 2014

(65) Prior Publication Data

US 2014/0267664 A1 Sep. 18, 2014

Related U.S. Application Data

(60) Provisional application No. 61/866,245, filed on Aug. 15, 2013, provisional application No. 61/788,619, filed on Mar. 15, 2013.

(51) Int. Cl.
| | |
|---|---|
| *G01J 3/50* | (2006.01) |
| *G06K 9/00* | (2006.01) |
| *G06T 7/40* | (2006.01) |
| *H04N 17/00* | (2006.01) |
| *A45D 44/00* | (2006.01) |
| *A61B 5/00* | (2006.01) |
| *G01J 3/46* | (2006.01) |
| *G06Q 50/22* | (2012.01) |

(52) U.S. Cl.
CPC ............ *G06K 9/00362* (2013.01); *G06T 7/408* (2013.01); *G06K 9/00221* (2013.01); *H04N 17/002* (2013.01); *A45D 44/005* (2013.01); *A61B 5/441* (2013.01); *G01J 3/463* (2013.01); *G01J 3/50* (2013.01); *G06K 9/00234* (2013.01); *G06Q 50/22* (2013.01)
USPC .............................................. 348/47; 356/364

(58) Field of Classification Search
None
See application file for complete search history.

(56) References Cited

U.S. PATENT DOCUMENTS

| | | | |
|---|---|---|---|
| 7,394,538 B2 * | 7/2008 | Bazin | ............................ 356/364 |
| 2003/0215471 A1 | 11/2003 | Wilmott et al. | |
| 2006/0210154 A1 * | 9/2006 | Leveque et al. | ............... 382/165 |

(Continued)

OTHER PUBLICATIONS

Annex to Form PCT/ISA/206 Communication Relating to the Results of the Partial International Search for International Patent Application No. PCT/US2014/028611, mailed Jul. 18, 2014, 2 pages.

(Continued)

*Primary Examiner* — Jay Au Patel
*Assistant Examiner* — Reza Aghevli
(74) *Attorney, Agent, or Firm* — Goodwin Procter LLP

(57) ABSTRACT

Systems and methods for determining a customized cosmetic formulation. In one method, a user is guided to capture an image of a skin region with known lighting and color characteristics, and the image is processed to provide calibrated skin color information. A customized cosmetic formulation is automatically determined for the user based on the calibrated skin color information. In another method, a user is interactively guided through capture of one or more skin region images using a device having an image sensor. The skin region images are processed to provide calibrated skin color information, which is compared to a ground truth data set to identify a set of closest known values in the ground truth data set. A customized cosmetic formulation is automatically determined for the user based on the comparison.

20 Claims, 11 Drawing Sheets

(56) References Cited

U.S. PATENT DOCUMENTS

| | | |
|---|---|---|
| 2007/0253987 A1 | 11/2007 | Wozniak et al. |
| 2010/0123801 A1* | 5/2010 | Son et al. .................. 348/231.99 |
| 2010/0245823 A1* | 9/2010 | Chhibber et al. ............. 356/366 |
| 2011/0211047 A1* | 9/2011 | Chhibber et al. ................ 348/47 |
| 2012/0229828 A1* | 9/2012 | Gill ................................ 358/1.9 |
| 2012/0237540 A1* | 9/2012 | Florence et al. ......... 424/195.17 |
| 2012/0251600 A1* | 10/2012 | Yu et al. ........................ 424/401 |

OTHER PUBLICATIONS

International Search Report and Written Opinion for International Patent Application No. PCT/US2014/028611, mailed Oct. 7, 2014, 15 pages.

\* cited by examiner

006
SYSTEMS AND METHODS FOR SPECIFYING AND FORMULATING CUSTOMIZED TOPICAL AGENTS

CROSS-REFERENCE TO RELATED APPLICATIONS

This application claims priority to and the benefit of U.S. Provisional Patent Application No. 61/788,619, filed on Mar. 15, 2013, and entitled "System and Method for Specifying and Formulating an Aesthetic and Protective Topical Agent Optimized for a Specific Use," and claims priority to and the benefit of U.S. Provisional Patent Application No. 61/866,245, filed on Aug. 15, 2013, and entitled "System and Method for Specifying and Formulating an Aesthetic and Protective Topical Agent Optimized for a Specific Use," the entireties of which are incorporated herein by reference.

TECHNICAL FIELD

The present disclosure relates generally to image analysis and topical agent formulation and, more specifically, to systems and methods for determining a customized cosmetic formulation based on color-calibrated skin images.

BACKGROUND

Aesthetic and protective cosmetic topical agents in the form of an applied cream or lotion are widely used to protect against UV radiation, provide a moisture barrier, mask blemishes and skin discoloration, reduce or prevent irritation, and provide other healthful and aesthetic benefits. In the best of all possible worlds, these protective topical agents would be specified by a team of experts for a particular individual with specific needs, and for a specific environment or use. The topical agent would then be formulated in a timely manner and delivered to the individual. Unfortunately, logistics and cost have to date limited the practicality of providing such a specific, optimized product to a given user.

Currently, there are several approaches to provide cosmetic topical agents that match a particular need. These agents may be compounded based on a specification from a dermatologist. They may be assembled in a retail store from a set of ingredients by a knowledgeable clerk. Systems or sets of cosmetic creams or lotions with a wide variety of properties may be pre-manufactured and chosen based on an given customer's coloration, skin type, and specific needs.

The main barrier to a general solution for the custom manufacture and distribution of these topical agents is that the number of features in the product are many, and the needs are quite varied. It is not commercially feasible to manufacture and stock each formulation with the granularity that is optimum for a given need and individual. What is needed, then, are ways to provide useful compounds based on a determination of an individual's specific needs using, for example, advanced image analysis techniques, and formulations that are optimal for that set of needs.

Techniques to capture the reflectance spectra of a surface with moderate specular reflectance and predominately diffuse reflectance can require measuring the reflected color as RGB triplets, or measuring the reflected spectra of the surface using optical methods to integrate the reflectance with a known light source at a known distance with a detector that has been set to a fixed aperture, fixed integration optics, and measured over a fixed period of time. Devices that use these techniques are reflection spectrophotometers and colorimeters.

Some mobile devices have many of the characteristics of the colorimeter. For instance, they have a light source with known characteristics, a CCD detector, a processor, and a lens system that can be used for integration. The primary barriers to using mobile devices as accurate colorimeters are the need to: (1) control ambient light; (2) set the distance to the surface to be sampled; (3) control the aperture used for measurement of the sample; (4) control the detector sensitivity used for measurement of the sample; (5) control the time used for measuring the sample; (6) control the white balance for measuring the sample; and (7) control the focal plane for measuring the sample.

While cameras used in mobile devices have become the most popular handheld cameras presently in use, they lack the ability to manually set aperture, and the most popular devices do not allow software to set aperture, sensitivity, or exposure times. While the hardware and firmware of the mobile device may report what camera settings are used as data embedded in a resulting digital image file, techniques are often used within the firmware to enhance or improve the image, and adjust the white balance. The firmware that controls the camera has been optimized to produce quality snapshots, not to make reliable measurement of light and color.

What is further needed, then, are systems and methods that address these issues and allow a user to capture accurate, repeatable color samples using a mobile device.

SUMMARY

Systems and methods are presented for determining customized cosmetic formulations and capturing accurate color information. In one aspect, a method of determining a customized cosmetic formulation includes guiding a user to capture an image of a skin region with known lighting and color characteristics; processing the image to provide calibrated skin color information; and automatically determining a customized cosmetic formulation for the user based on the calibrated skin color information. The skin region image can be received from a device having an image sensor, and the user can be interactively guided through capture of a plurality of skin region images, such as facial regions, using the device image sensor.

In one implementation, the user is interactively guided through capture of an image of a marker using the device image sensor, and the skin region image is processed based at least in part on the captured marker image. The device can be a mobile phone, a tablet, a digital camera, a webcam, smart glasses, a television, or a gaming console. The skin region image can include embedded data identifying properties of at least one of the device and the image sensor, and the skin region image can be processed based at least in part on the embedded data.

In another implementation, automatically determining the customized cosmetic formulation includes matching the calibrated skin color information to a reference user, the reference user having a previously determined cosmetic formulation associated therewith. The automatic determination of the customized cosmetic formulation can be based at least in part on an indication by the user of an allergy to a cosmetic ingredient. A topical agent based on the customized cosmetic formulation can be compounded and delivered to the user. The user can be allowed to purchase a topical agent compounded based on the customized cosmetic formulation.

In another aspect, a system for determining a customized cosmetic formulation includes at least one computer that itself includes a memory for storing computer-executable instructions and a processing unit for executing the instructions stored in the memory. The execution of the instructions configures the computer to perform operations including guiding a user to capture an image of a skin region with known lighting and color characteristics; processing the image to provide calibrated skin color information; and automatically determining a customized cosmetic formulation for the user based on the calibrated skin color information. The skin region image can be received from a device having an image sensor, and the operations can further include interactively guiding the user through capture of a plurality of skin region images, such as facial regions, using the device image sensor.

In one implementation, the operations further include interactively guiding the user through capture of an image of a marker using the device image sensor, and the skin region image is processed based at least in part on the captured marker image. The device can be a mobile phone, a tablet, a digital camera, a webcam, smart glasses, a television, or a gaming console. The skin region image can include embedded data identifying properties of at least one of the device and the image sensor, and the skin region image can be processed based at least in part on the embedded data.

In another implementation, automatically determining the customized cosmetic formulation includes matching the calibrated skin color information to a reference user, the reference user having a previously determined cosmetic formulation associated therewith. The automatic determination of the customized cosmetic formulation can be based at least in part on an indication by the user of an allergy to a cosmetic ingredient. The operations can further include allowing the user to purchase a topical agent compounded based on the customized cosmetic formulation.

In one aspect, a method of determining a customized cosmetic formulation includes interactively guiding a user through capture of one or more images using a device having an image sensor, each image comprising a skin region of the user; processing the skin region images to provide calibrated skin color information; comparing the calibrated skin color information to a ground truth data set to identify a set of closest known values in the ground truth data set; and automatically determining a customized cosmetic formulation for the user based on the comparison. The customized cosmetic formulation includes at least one of (i) a unique compound that is derived based on a relative proximity of the calibrated skin color information to the set of closest known values and (ii) an existing cosmetic product.

In one implementation, processing the skin region images includes, for at least one of the skin region images: detecting a plurality of facial regions in the at least one skin region image; segmenting the facial regions based on skin tone; and assigning a color to each facial region segment based on at least one of skin tone, shadow, and specular highlight.

In another implementation, ambient lighting information associated with at least one of the skin region images is received, and the at least one skin region image is processed based at least in part on the ambient lighting information.

In a further implementation, the method further includes interactively guiding the user through capture of an image of a marker using the device image sensor, and the skin region images are processed based at least in part on the marker image. The current settings of the device image sensor can be stored based on a successful capture of the marker image. The device image sensor settings can include exposure, focus, and/or white balance. The skin region images can be processed based on the stored image sensor settings. Processing the skin region images can include compensating for unknown light sources.

In yet another implementation, the skin region is a wrist, a forehead, a left cheek, a right cheek, and/or a full face. The method can further include allowing the user to purchase the existing cosmetic product. The device can be a mobile phone, a tablet, a digital camera, a webcam, smart glasses, a television, and/or a gaming console.

In another aspect, a system for determining a customized cosmetic formulation includes at least one computer that itself includes a memory for storing computer-executable instructions and a processing unit for executing the instructions stored in the memory. The execution of the instructions configures the computer to perform operations including interactively guiding a user through capture of one or more images using a device having an image sensor, each image comprising a skin region of the user; processing the skin region images to provide calibrated skin color information; comparing the calibrated skin color information to a ground truth data set to identify a set of closest known values in the ground truth data set; and automatically determining a customized cosmetic formulation for the user based on the comparison. The customized cosmetic formulation includes at least one of (i) a unique compound that is derived based on a relative proximity of the calibrated skin color information to the set of closest known values and (ii) an existing cosmetic product.

In one implementation, processing the skin region images includes, for at least one of the skin region images: detecting a plurality of facial regions in the at least one skin region image; segmenting the facial regions based on skin tone; and assigning a color to each facial region segment based on at least one of skin tone, shadow, and specular highlight.

In another implementation, ambient lighting information associated with at least one of the skin region images is received, and the at least one skin region image is processed based at least in part on the ambient lighting information.

In a further implementation, the operations further include interactively guiding the user through capture of an image of a marker using the device image sensor, and the skin region images are processed based at least in part on the marker image. The current settings of the device image sensor can be stored based on a successful capture of the marker image. The device image sensor settings can include exposure, focus, and/or white balance. The skin region images can be processed based on the stored image sensor settings. Processing the skin region images can include compensating for unknown light sources.

In yet another implementation, the skin region is a wrist, a forehead, a left cheek, a right cheek, and/or a full face. The operations can further include allowing the user to purchase the existing cosmetic product. The device can be a mobile phone, a tablet, a digital camera, a webcam, smart glasses, a television, and/or a gaming console.

In one aspect, a method of capturing accurate color of an object using a device having an image sensor includes calibrating a plurality of settings of the device using a marker having a known size; measuring a color of each of a plurality of surfaces of the object; determining a surface reflectance of the object based on the measured colors; and determining a surface color variation of the object based on the calibrated settings, the measured surface colors, and the surface reflectance of the object. The plurality of surfaces can include regions of skin, and the device can be a mobile phone, a tablet, a digital camera, a webcam, smart glasses, a television, or a gaming console. The marker can have a known reflectance.

In one implementation, calibrating the device includes directing a user to place the marker on a substantially white field. Calibrating the device can include setting, based on a captured image of the substantially white field, at least one of aperture, sensitivity, exposure time, and white balance of the device. Calibrating the device can also include setting a light associated with the device image sensor to a known brightness. Further, calibrating the device can include interactively guiding a user to position the device image sensor at a specific distance from a surface of the marker. Moreover, calibrating the device can include, upon the positioning of the device image sensor at the specific distance from the surface of the marker, locking at least one of the settings of the device. The settings of the device can be automatic exposure, automatic focus, and/or automatic white balance. The locked settings of the device can be applied while measuring the color of each of the surfaces of the object.

In another implementation, measuring a color of a surface of the object includes directing a user to place the marker in proximity to the surface of the object. Measuring a color of a surface of the object can also include interactively guiding a user to position the device image sensor and the object relative to one another to match a calibration target. The interactive guidance can include voice direction. Measuring a color of a surface of the object can further include, upon a positioning of the device image sensor at a specific distance from the marker, capturing a color of the surface of the object.

In a further implementation, determining the surface reflectance of the object includes transforming the captured color to a surface reflectance of the object.

In another aspect, a system for capturing accurate color of an object includes at least one computer that itself includes a memory for storing computer-executable instructions and a processing unit for executing the instructions stored in the memory. The execution of the instructions configures the computer to perform operations including calibrating a plurality of settings of a device (which can have an image sensor) using a marker having a known size; measuring a color of each of a plurality of surfaces of the object; determining a surface reflectance of the object based on the measured colors; and determining a surface color variation of the object based on the calibrated settings, the measured surface colors, and the surface reflectance of the object. The plurality of surfaces can include regions of skin, and the device can be a mobile phone, a tablet, a digital camera, a webcam, smart glasses, a television, or a gaming console. The marker can have a known reflectance.

In one implementation, calibrating the device includes directing a user to place the marker on a substantially white field. Calibrating the device can include setting, based on a captured image of the substantially white field, at least one of aperture, sensitivity, exposure time, and white balance of the device. Calibrating the device can also include setting a light associated with the device image sensor to a known brightness. Further, calibrating the device can include interactively guiding a user to position the device image sensor at a specific distance from a surface of the marker. Moreover, calibrating the device can include, upon the positioning of the device image sensor at the specific distance from the surface of the marker, locking at least one of the settings of the device. The settings of the device can be automatic exposure, automatic focus, and/or automatic white balance. The locked settings of the device can be applied while measuring the color of each of the surfaces of the object.

In another implementation, measuring a color of a surface of the object includes directing a user to place the marker in proximity to the surface of the object. Measuring a color of a surface of the object can also include interactively guiding a user to position the device image sensor and the object relative to one another to match a calibration target. The interactive guidance can include voice direction. Measuring a color of a surface of the object can further include, upon a positioning of the device image sensor at a specific distance from the marker, capturing a color of the surface of the object.

In a further implementation, determining the surface reflectance of the object includes transforming the captured color to a surface reflectance of the object.

Other aspects and advantages of the invention will become apparent from the following drawings, detailed description, and claims, all of which illustrate the principles of the invention, by way of example only.

BRIEF DESCRIPTION OF THE DRAWINGS

A more complete appreciation of the invention and many attendant advantages thereof will be readily obtained as the same becomes better understood by reference to the following detailed description when considered in connection with the accompanying drawings. In the drawings, like reference characters generally refer to the same parts throughout the different views. Further, the drawings are not necessarily to scale, with emphasis instead generally being placed upon illustrating the principles of the invention.

DETAILED DESCRIPTION

Described herein are various implementations of systems and methods for specifying and formulating topical agents that are optimized for the characteristics of particular individuals using, for example, image analysis techniques applied to photographs taken with mobile phones, tablets, webcams, digital cameras, gaming consoles, televisions, smart glasses, and other consumer or professional devices that have an image sensor.

Optimized Aesthetic Protective Topical Agent

In one implementation, a system is provided that generates a specification for a customized topical agent, referred to herein as the "Optimized Aesthetic Protective Topical Agent," abbreviated as "OAPTA." The OAPTA is formulated for the needs and characteristics of a specific individual client, referred to herein as the "User." The OAPTA can include a set of possible components. The set can be large enough to meet most needs of a given User. In some instances, only a small number of components are used in a specific formulation of an OAPTA for a User. The components of the OAPTA (an OAPTA Component Set) can include, but are not limited to:

1. Topical bases, water, emulsion, gel, gum.
2. Moisture agents.
3. Ultraviolet (UV) filtering agents.
4. Opacity (hiding) agents.
5. Color control agents.
6. Reflectance (shine, matte, opalescence) control agents.
7. Anti-inflammatory agents (e.g., aloe, etc.).
8. Protective agents (e.g., vitamin E, etc.)

OAPTA Service

Figure 1:
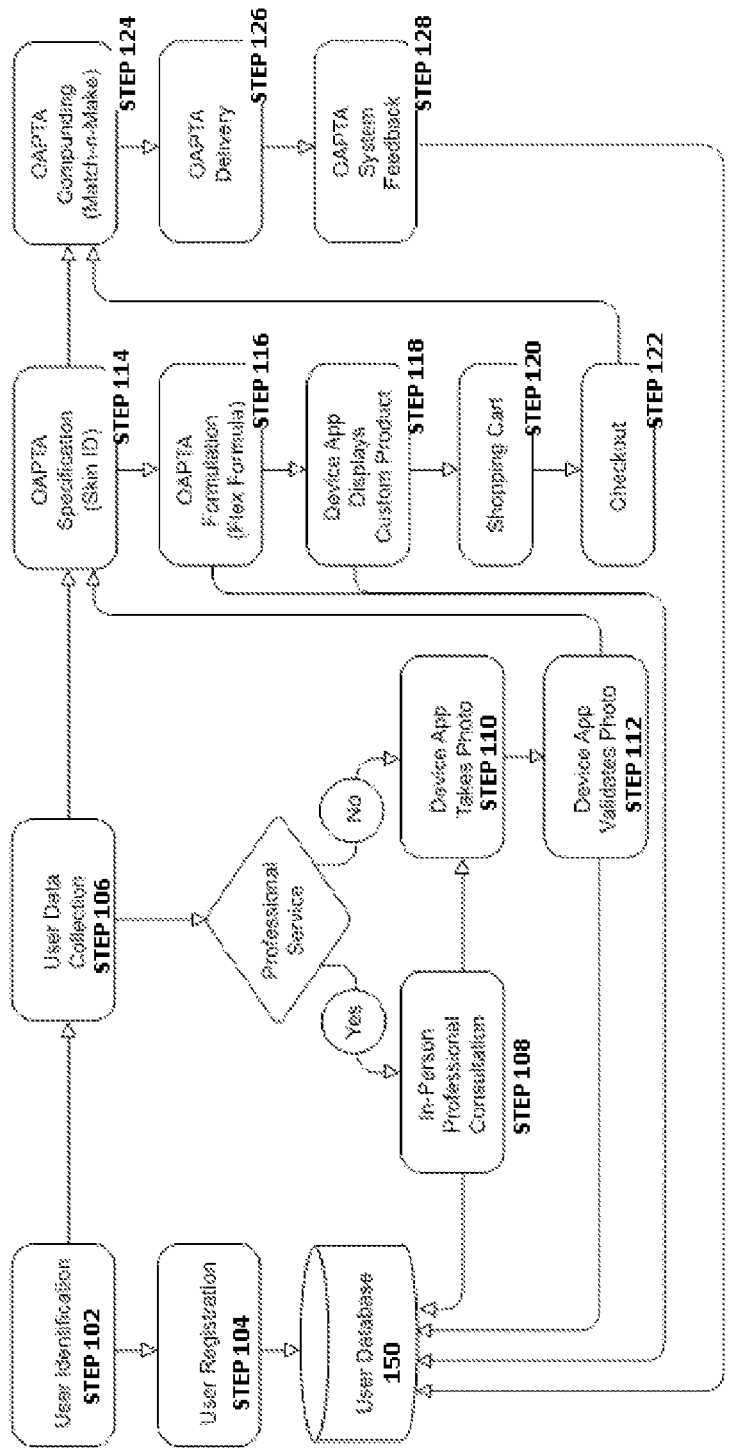
FIG. 1 is a flowchart of an example method for providing an optimized topical agent to a user according to an implementation of the invention.
Figure 2:
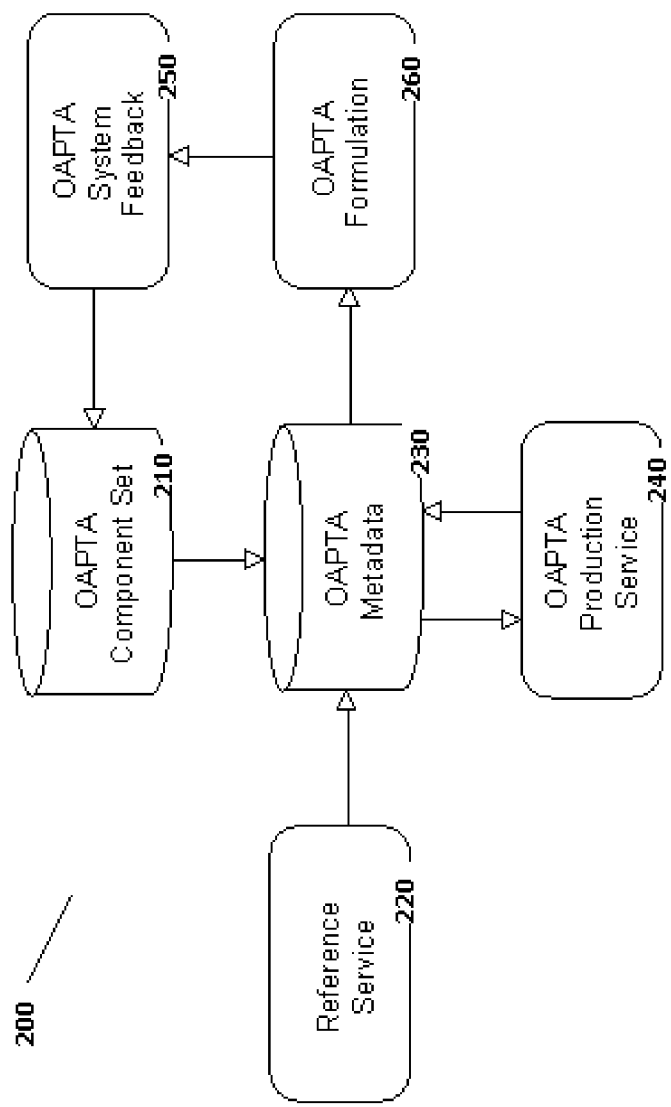
FIG. 2 is a high-level architecture diagram of an example system for providing an optimized topical agent to a user according to an implementation of the invention.

Referring to FIG. 1, in one implementation, the OAPTA is provided to the User using the following high-level steps. For the sake of brevity and clarity, the aggregation of all the steps to provide an OAPTA to a User will be referred to as a "Service" herein. In STEP 102, the User is identified using, for example, a user name and password that provides access to the present system. In the case that the User has not previously used the system, the User can proceed to registration to set up a new account (STEP 104). The User's details (e.g., name, address, etc.) can then be stored in User Database 150. Once the User is identified by the system (e.g., logged in), data can be collected (STEP 106) to determine the User's needs (e.g., allow the user to indicate desired cosmetics, allow the user to specify any allergies, capture skin imagery, and so on). The data collection step can be performed using a professional service, such as an in-person professional consultation (STEP 108) or, alternatively, can be performed by Users themselves by taking a photograph using an application on a consumer device (e.g., a mobile phone, tablet, or other device) (STEP 110), which will then automatically validate the photograph for color accuracy, quality, and other properties (STEP 112). Information captured by the professional service and/or the device application can be stored in the User Database 150 for later reference and reuse.

Following data collection (or reference to previously collected data), STEP 114 provides for the OAPTA Specification, in which the components of the OAPTA are specified using components such as those described above. In STEP 116, based on the OAPTA Specification, the instructions to formulate and/or manufacture the OAPTA are generated. If the User is using an application to generate the OAPTA, the application can display the custom product to be created (STEP 118), and allow the User to place the product in a shopping cart (STEP 120) and purchase it (STEP 122). The generated formulation instructions can then be used to compound the OAPTA or select a premade OAPTA that matches the formula (STEP 124). The OAPTA can then be delivered to the User (STEP 126), and feedback can optionally be collected to determine if the User's need were met (STEP 128).

OAPTA System

In one implementation, the system 200 that provides the OAPTA to Users is made up of a set of components and Services. The system 200 can include a shared OAPTA Component Set 210, such as that described above, for use by the various OAPTA Services in the system 200. At least one OAPTA Reference Service 220 can facilitate the creation of an OAPTA for a collection of reference uses and the assembly of OAPTA Metadata 230. The OAPTA Reference Service 220 collect user data in the same manner as the OAPTA Production Service 240, and can collect additional user data to formulate an optimal OAPTA Specification.

The OAPTA Metadata 240 is the assembly of user data collected from an OAPTA Reference Service 220 in a form that allows for the mapping of user data collected from the OAPTA Production Service 240 to the OAPTA specifications generated by the OAPTA Reference Service 220. At least one OAPTA Production Service 240 provides for the creation of the OAPTA Specification using the OAPTA Metadata 230 generated by at least one OAPTA Reference Service 220. OAPTA System Feedback 250 provides for the collection of OAPTA Feedback from at least one OAPTA Reference Service 220 and at least one OAPTA Production Service 240, in order to modify or change a OAPTA Component Set 210 and/or modify the Specification, Formulation and Compounding 260 of the OAPTA Production Service 240.

Shared OAPTA Component Set

The Shared OAPTA Component Set 210 can be specified as described below; yet it is to be appreciated that the Shared OAPTA Component Set 210 can be specified in various suitable manners that function similarly within the OAPTA system described herein. A group composed of a Dermatologist, an Esthetician, and a cosmetic Colorist is referred to herein as an "OAPTA Professional Group." In one implementation, the Shared OAPTA Component Set 210 is specified by the OAPTA Professional Group. The Shared OAPTA Component Set 210 can be specified first as a full set, and then as a set of connections indicating those components that can be used with one another. For instance, a set of colorants can be specified as only usable with a specific topical base, or a group of components that work together to provide more opacity cam be indicated as most effective when used together. Similarly, groups of those items which are best for Users with certain allergies can be identified and tagged.

This initial mapping of components provides data for the Specification method of the OAPTA Production Service 240, and will be referred to herein as the "Specification Hints." In one implementation, the Specification Hints are represented as a non-directed graph, which is converted to a set of minimum spanning trees. It is to be appreciated that it is faster to traverse a minimum spanning tree to discover which components can be used together, rather than evaluating a non-directed graph. After this conversion, a single item in the Shared OAPTA Component Set 210 can be referenced by multiple spanning trees which compose the Specification Hints. After initial creation, the Specification Hints can be updated or discovered by OAPTA System Feedback 250, as well as modified by the OAPTA Professional Group.

OAPTA Reference Service

The OAPTA Reference Service 220 can be constructed after the Shared OAPTA Component Set 210 is specified. The OAPTA Reference Service 220 produces the OAPTA Metadata 230 needed to construct the OAPTA Production Service 240. In one implementation, the OAPTA Reference Service 220 is configured as a professional service. In another implementation, the OAPTA Reference Service 220 is configured as an online business and a retail store. The implementation of the OAPTA Reference Service 220 as a professional service is used as an example in the description below.

Reference User Identity

As a professional service, the OAPTA Reference Service 220 can use best practices for managing a User Identity. In addition to this, it can also implement a privacy policy and information use policy that allows the Reference Service 220 to collect and store User data in a form that is anonymous and does not identify the User, and that can be used to build OAPTA Metadata 230. Agreements can also be made, based on some consideration, for the data to be used by the OAPTA system 200 so that a user of the production component of the system 200 can identify a specific Reference User (such as a celebrity) that has a similar OAPTA product need.

Reference User Data Collection

The OAPTA Reference Service 220 can use the same data collection as the OAPTA Production Service 240. In addition, this data can be augmented with collection methods as specified by the OAPTA Professional Group.

Common Service Data Collection

In one implementation, the Service data collection uses an application on a set of mobile devices that have similar features and are manufactured in a manner to have similar information gathering and media display properties. The mobile application can walk the User through a series of steps to collect the data. For example, the application can ask the User if he or she has specific needs or allergies. The application can show a video instructing the User what step to perform next, and/or can use the context of a mobile game to obtain and optimize the data. The mobile device can be selected, and the application constructed, to provide consistent data from each collection. Consistent image data collection can be performed using one or more of the following methods.

1. In one example, a manufactured token or marker with known characteristics (e.g., a portion of a new dollar bill, a new quarter, or a marker which is manufactured and sent to the user) is used. A mobile device application can instruct the User to take a picture of a portion of the marker alone and/or the marker next to the User's skin. The image is sent to the OAPTA Service, where it is calibrated based on the marker used, and the necessary data is generated from the image.

2. In another example, a reference color chart is projected on the User device screen and the User is instructed to take a picture in the mirror capturing both her skin and the reference color chart in the same frame. The image is sent to the OAPTA Service, where it is calibrated based on the marker used, and the necessary data is generated from the image.

3. In a further data collection example, a mobile device's internal flash is used as a light source, and the User is instructed to take a picture of her skin in a specific manner. The image is sent to the OAPTA service, where it is calibrated based on the flash and Exif data from the device, including focal length, and the necessary data is generated from the image.

4. In another example, packaging used to ship OAPTA products is designed in a manner to hold a mobile device to provide a light shield and define a specific distance from the User's skin. The user is instructed to take a picture of her skin in a specific manner. The image is sent to the OAPTA data collection service, where it is calibrated based on the flash and Exif data from the device, including focal length, and the necessary data is generated from the image.

5. In yet another example, an image can be captured by an application on a mobile device that allows software to control the camera. The software running on the device can set the device to use only a flash or light resident on the device, and/or it can also use facial detection on the device to time when an image is taken. The image can be taken when, for example, the distance to the User's face is within a known distance and/or the User's face is centered and in focus. The software running on a mobile device can also use real-time video capture to determine the amount of ambient light (not using the flash) and can use a voice or text prompt to interactively suggest to the User how to change the lighting. Information about the ambient lighting detected in video mode before the digital photo is taken with the flash can be sent along with the image for processing. Additionally, two images can be taken in quick succession, one with ambient light and one with flash.

Figure 3A:
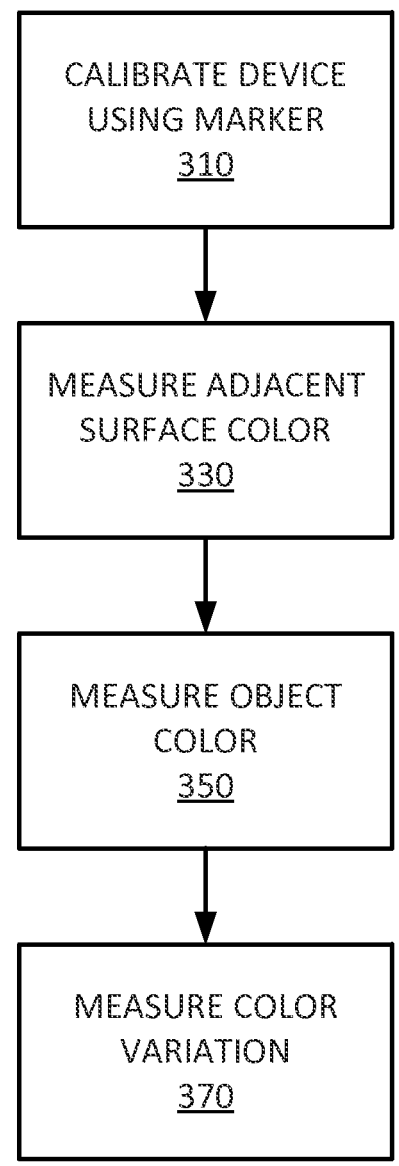
FIGS. 3A-3D are flowcharts of example methods for capturing skin color using a device with an image sensor according to implementations of the invention.

Capturing accurate skin color using the camera and light on a mobile device will now be described in further detail. It is to be appreciated that, although the present techniques are described primarily with respect to capturing accurate skin color, other applications are possible, particularly in circumstances where one would use a colorimeter. FIG. 3A depicts one implementation of a process for capturing skin color using a mobile device or other device with an image sensor. In STEP 310, the device is calibrated using a marker of known size on a white or substantially white field. In STEP 330, the system measures the color of an object's surface (e.g., a skin region) adjacent to the marker. In STEP 350, the color of an object of known size is measured and, in STEP 370, the system measures the color variation of an object's surface based on the luminance found in STEP 330 and/or STEP 350.

Figure 3B:
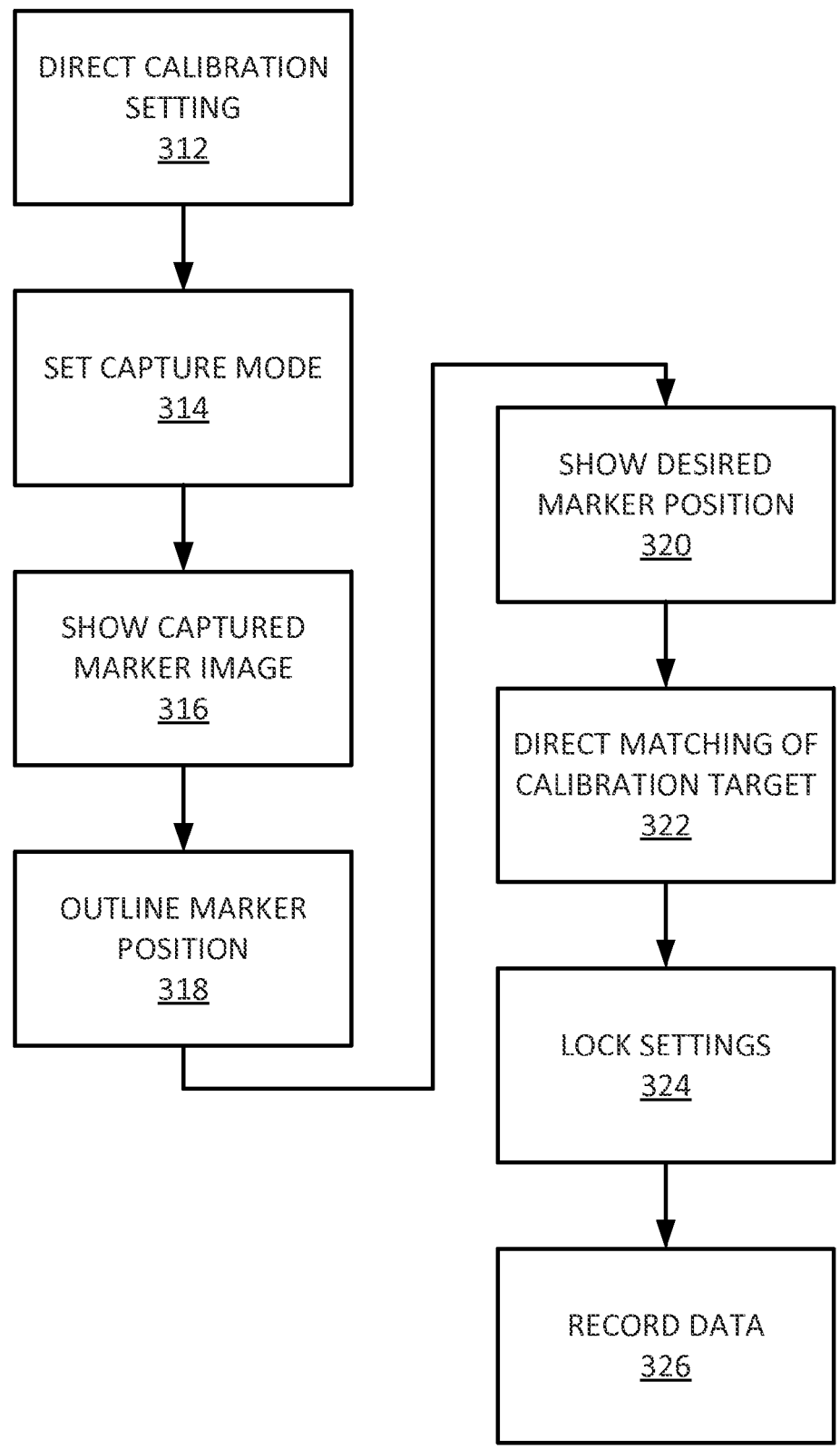

Referring now to FIG. 3B, the device calibration STEP 310 is shown in further detail. In some implementations, calibrating the device requires a setting where a software detectable object of known size and known reflectance (a "marker") is placed on a white or substantially white field. This setting can be manufactured, and can be, for instance, a portion of product packaging, or included within a packaged product, such as a skin care product. Alternatively, this setting can be created by placing a common object or an object having well-known properties, such a coin, on a white field or substantially white field with known properties, such as two sheets of copier/printer paper. The distance used for calibration can be determined to be close enough to the measured surface to reduce the effect of ambient light.

In STEP 312, a software application on the device directs the User set to place or construct the setting used for calibration. The software can set a specific video or image capture mode for a camera on the device, and set the light associated with the camera to a known brightness (STEP 314). The software on the device can interactively show the captured image of the marker on the field (STEP 316), and can detect the marker and highlight or outline the marker's position for the User (STEP 318). In some implementations, the marker's position is offset so that the software uses the white field to set the aperture, sensitivity, exposure time, and white balance of the device.

In STEP 320, the software shows or highlight the desired size and position for the marker that will result in the device's camera being positioned at a specific distance. This size and position is referred to herein as the "calibration target." The software can interactively direct the User to match the highlighted marker with the calibration target (STEP 322). When the User positions the device to match the marker with the calibration target, the software can cause the device to lock automatic exposure, automatic focus, and automatic white balance (STEP 324). This locking effectively calibrates aperture, sensitivity, shutter speed, focus, and white balance to a predetermined distance to a surface with known reflectance. The white point (and other data) of the setting can be recorded and used to calibrate subsequent sessions (STEP 326).

Figure 3C:
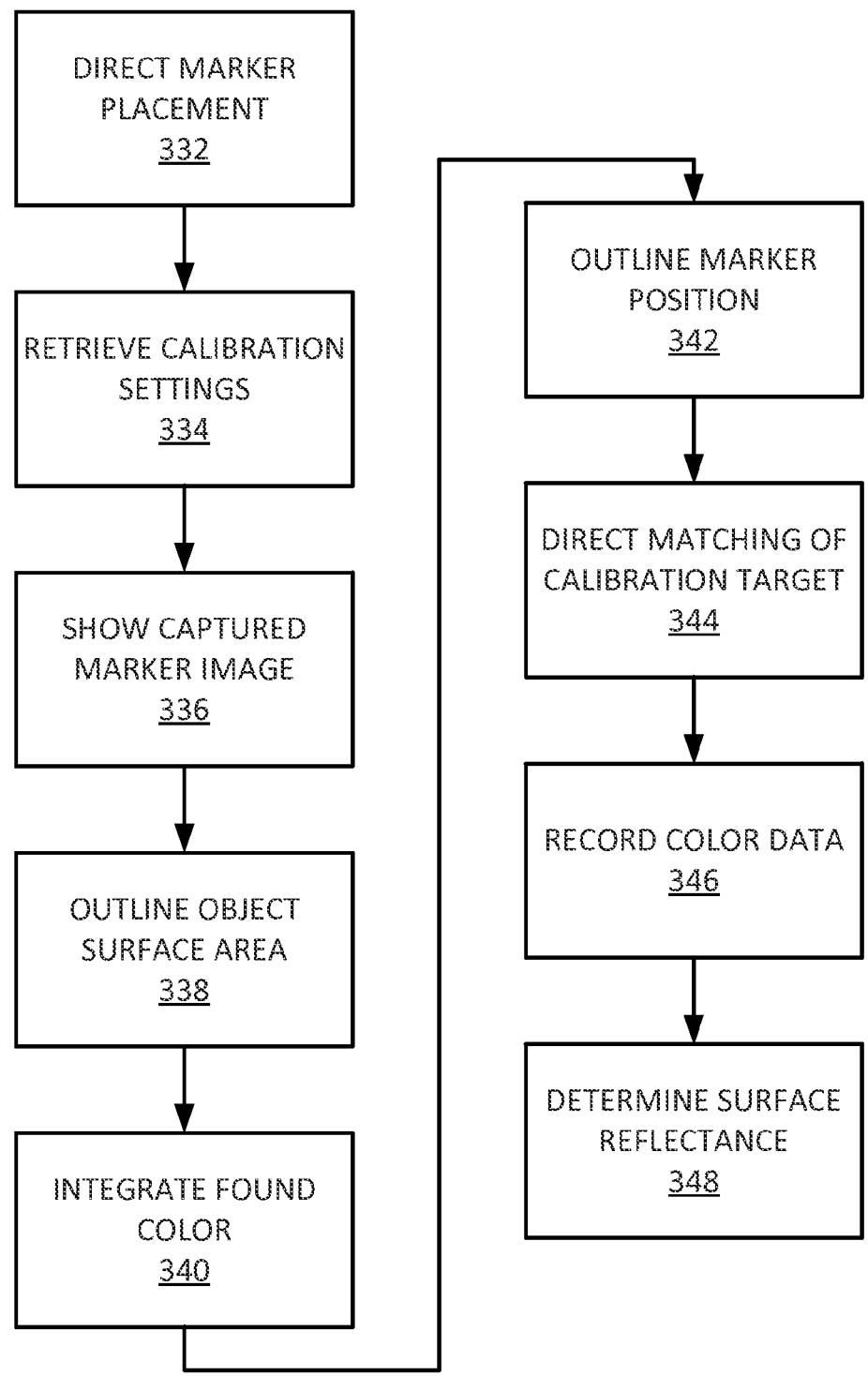

Referring now to FIG. 3C, the adjacent surface color measurement STEP 330 is shown in further detail. In one implementation, measuring the color of an object necessitates that the distance from the device's camera to the surface of the object's surface be set, or at least known. If the object size is not fixed, this can be done by placing a marker of the same used in the calibration step adjacent to the surface to be measured.

In STEP 332, the software on the device directs the user to place the marker adjacent to or on the surface to be measured. In STEP 334, the software maintains or recreates the locked settings from the calibration step 310. The software can interactively show the captured image of the marker adjacent to the object (STEP 336), including showing an outline of the area of the object's surface being integrated and measured (i.e., the "swatch") (STEP 338). In STEP 340, the software can integrate the color found in the swatch are and show the found color interactively. The software can also detect the marker and highlight or outline the marker's position for the user interactively (STEP 342). The marker's position can be offset so that the swatch matches the region of the captured image used to calibrate the white point.

In STEP 344, the software interactively directs the user to match the highlighted marker with the calibration target. When the user positions the device to match the marker with the calibration target, the software can record the integrated color of the swatch as the raw color value of the object (STEP 346). The software can use known techniques to apply the found white balance and stored data about the characteristic of the device to transform the found raw color value of the object to the surface reflectance of the object (STEP 348).

Figure 3D:
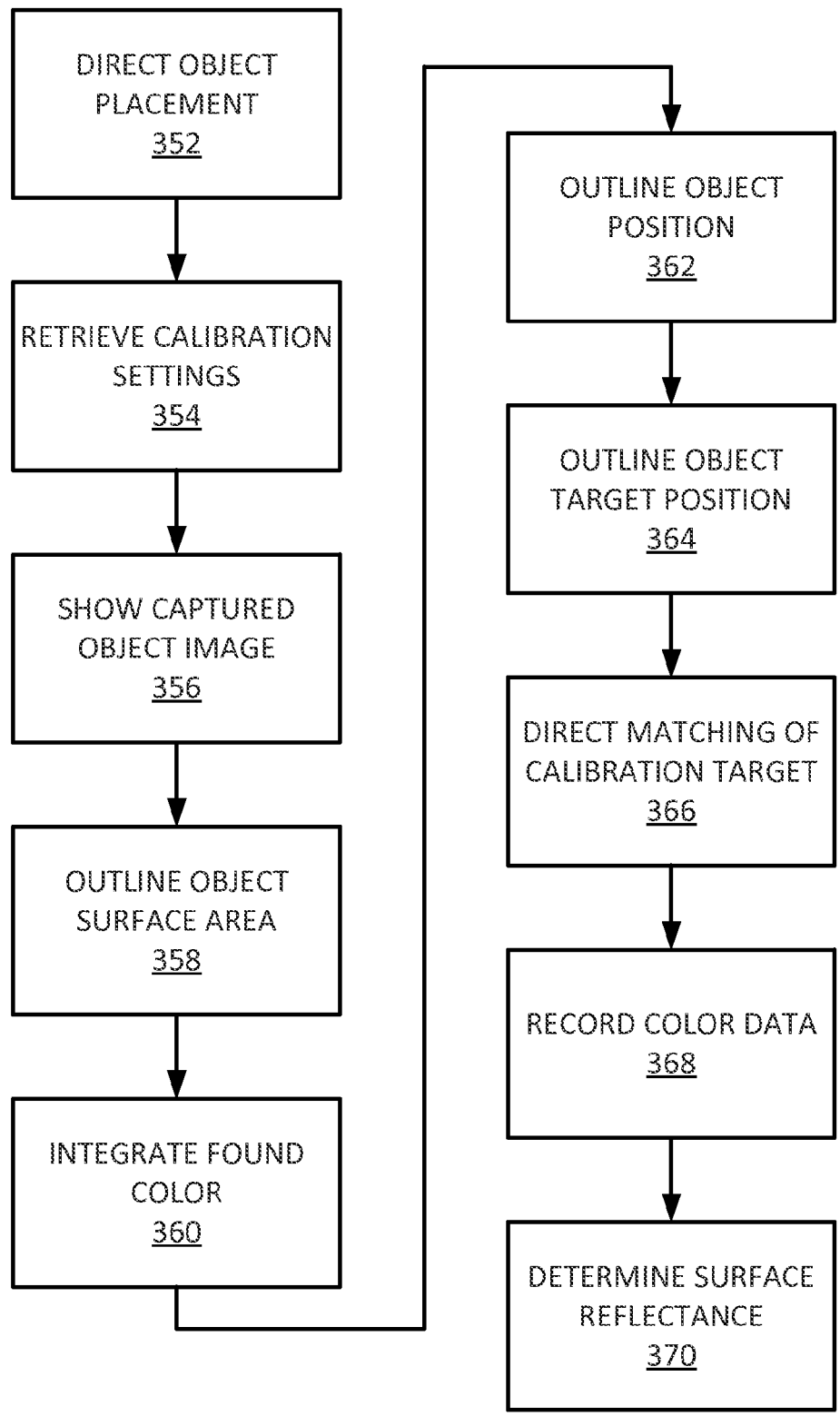

Referring now to FIG. 3D, the object color measurement STEP 350 is shown in further detail. If the object to be measured has a known size, or features of a known size, the size of these features can be used to determine the distance of the device's camera to the object to be measured. For instance, in measuring skin color, the width of a User's wrist, or the distance between the User's pupils can be used to detect the distance of the device's camera to the User's skin.

In STEP 352, the software on the device directs the user to point the camera at the object (e.g., wrist, face, cheek, forehead, or other skin region), and to hold the object in a position to match an outline on the display. In STEP 354, the software maintains or recreates the locked settings from the calibration step 310. The software can interactively show the captured image of the wrist or other object, and highlight the found width of the wrist (STEP 356). The software can further show an outline of the area of the object's surface being integrated and measured (i.e., the swatch) (STEP 358). In STEP 360, the software can integrate the color found in the swatch are and show the found color to the User interactively.

The software can detect the marker and highlight or outline the wrist's position for the User interactively (STEP 362), and can also interactively highlight or outline the wrist's target position for matching the calibration distance (STEP 364). The software can further interactively direct the User to match the highlighted marker with the calibration target (STEP 366). When the User positions the device to match the wrist with the wrist's target, the software can record the integrated color of the swatch as the raw color value of the wrist (STEP 368). In STEP 370, the software can use known techniques to apply the found white balance and stored data about the characteristic of the device to transform the found raw color value of the wrist to the surface reflectance of the object.

Referring back now to STEP 370 in FIG. 3A, an object's surface color variation can be measured when the overall reflectance of the object is known, the device has been calibrated, and the color of a portion of the object is known. For instance, if the color of a person's inside and outside wrist is known, and the color of a person's forehead is detected using intra pupillary distance, variation in skin tone can be measured by positioning the device such that the integrated reflectance matches a known value.

Facial Region Detection

Figure 4A:
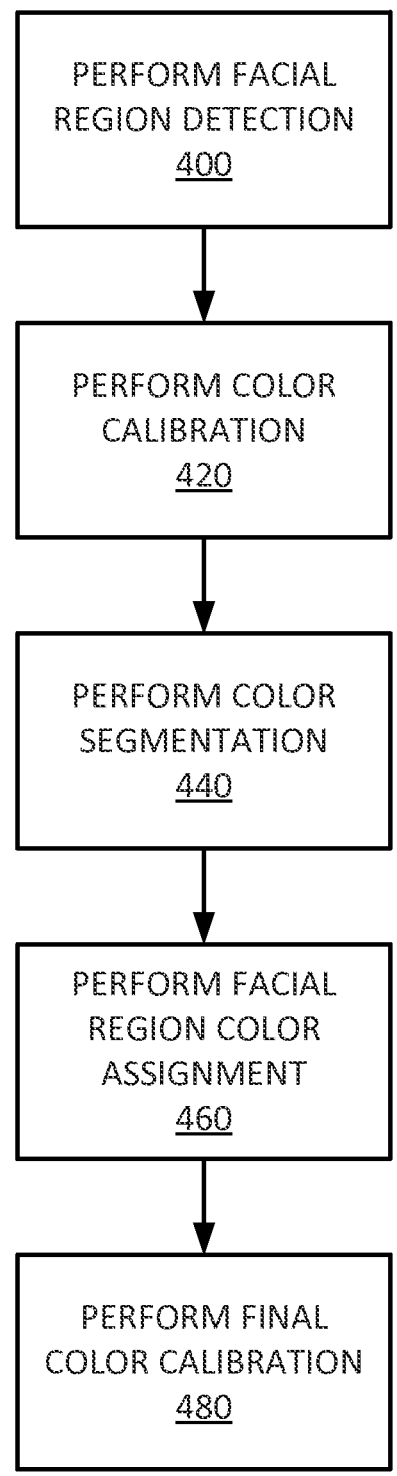
FIGS. 4A-4E are flowcharts of example methods for analyzing an image containing a facial region according to implementations of the invention.

In one implementation, the present system performs processing on an image containing a User's face or a portion of the User's face as part of formulating a customized topical agent for the User. As shown in FIG. 4A, facial region detection is performed on the image (STEP 400), and calibrated color and reflectance information is provided (STEP 420). Color segmentation (STEP 440), facial region color assignment (STEP 460), and final facial region color calibration (STEP 480) can also be performed, as further described below.

In some implementations, once an image is received by the OAPTA data collection service, it is processed to provide calibrated color and reflectance information. To assist in the calibration process, a facial region detection process (STEP 400) can be used. For example, open source and other techniques exist to detect the position of the face, eyes, mouth and nose in a digital photo. For reference, a Haar Cascade Classifier can be used with training sets built for detecting facial features. One software package and associated training sets that can be used to provide this functionality is found at OpenCV (opencv.org).

Using the positions of the facial features determined by a suitable procedure such as those described above, existing open source and other techniques can be used to detect the position of discrete facial features in the digital photo. For reference, active shape models developed with a large training set can be used. One software package and associated data that can be used to prove this functionality is the stasm library.

Figure 4B:
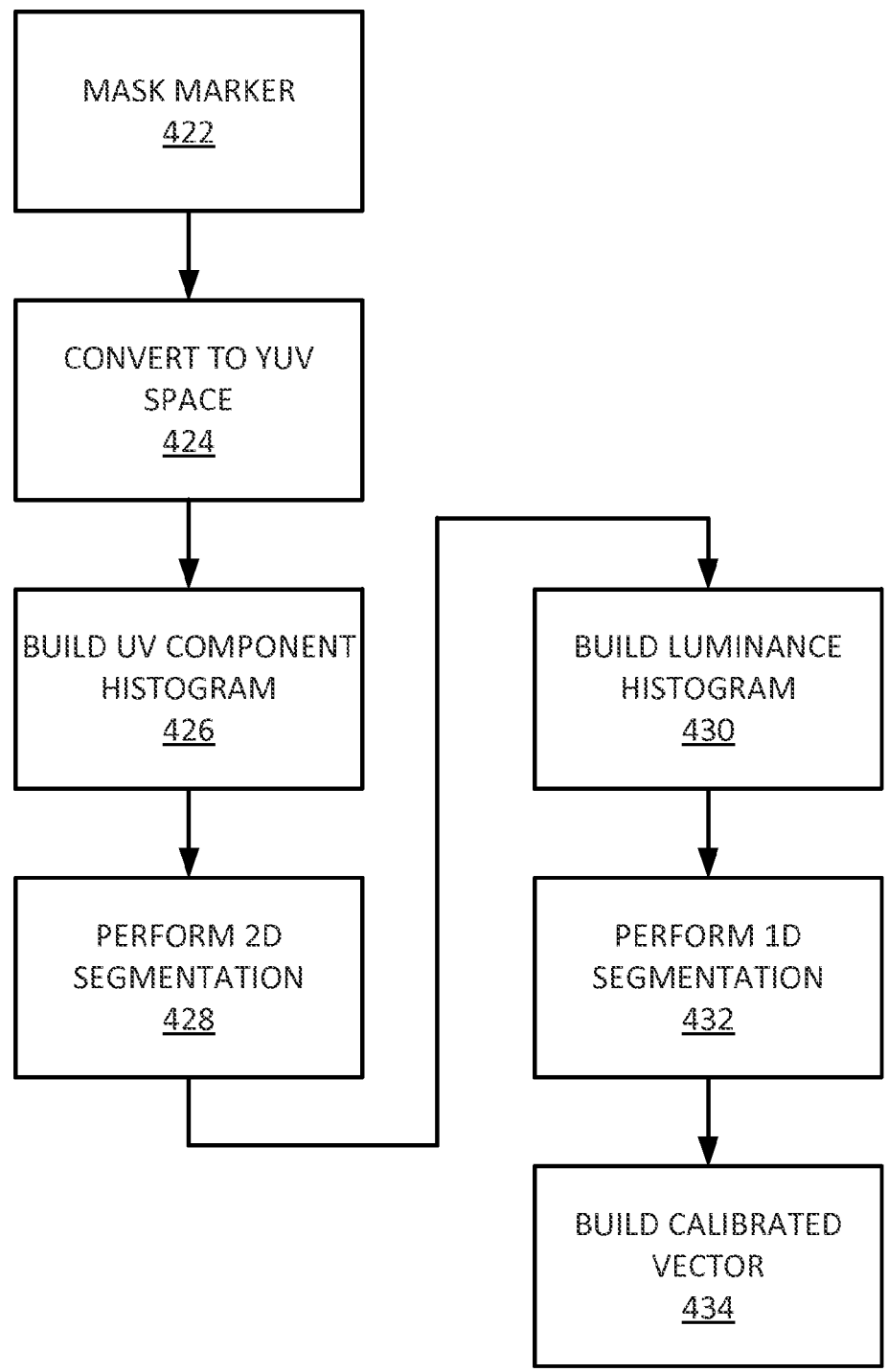

The discrete facial feature points determined above can then be assembled into a set of polygonal regions. In one implementation, the face includes 77 recognized feature points, although any suitable number of feature points and regions can be used. The recognized regions can include, but are not limited to:

Face (includes all regions)
Forehead
Right cheek
Left cheek
Nose
Nose bridge
Mouth (includes both lips)
Chin
Right eyebrow
Left eyebrow
Right eye
Left eye
Top lip
Bottom lip
Color Calibration FIG. 4B depicts STEP 420 in further detail, namely, one implementation of a method to provide calibrated color and reflectance information using a captured image. In STEP 422, the image is calibration, and the marker, if used, is recognized and masked. The image is converted into YUV color space (STEP 424) and a 2D histogram of the UV image components is built (STEP 426). In the following STEP 428, 2D segmentation is performed on the UV histogram to find a set of colors representing highlight, body color and spot color. A luminance histogram of the Y image component is built (STEP 430), and 1D segmentation is performed on the luminance histogram to find a luminance set representing reflectance of body color, amplitude of highlight reflection (shininess) and shadow luminance (STEP 432). Then, in STEP 434, a calibrated n-dimensional vector is built using the combined UV and luminance sets. This vector is referred to hereinafter as the "nColorVector." Of note, the nColorVector can contain data representing skin shininess and color variation (spottedness).

In another implementation, a digital photo can be calibrated based at least in part on data embedded in a digital photograph, such as the IFD tags found in JPEG compression, or Exchangeable image file format (Exif) data. The characteristics of the device used to take the photograph can be used to pre-calibrate the color. The distance from the camera to the User's face can be determined by the inter-ocular distance found by facial feature detection, such as that described herein. The shot data embedded in the digital photo, such as brightness, flash characteristics, and so on, can be combined with the distance from the camera to adjust the luminance of the image. Further, additional data sent by software resident on the device at the time of the shot, such as ambient lighting information or an ambient lighting image, can be used to color correct for ambient lighting.

Color Segmentation

Figure 4C:
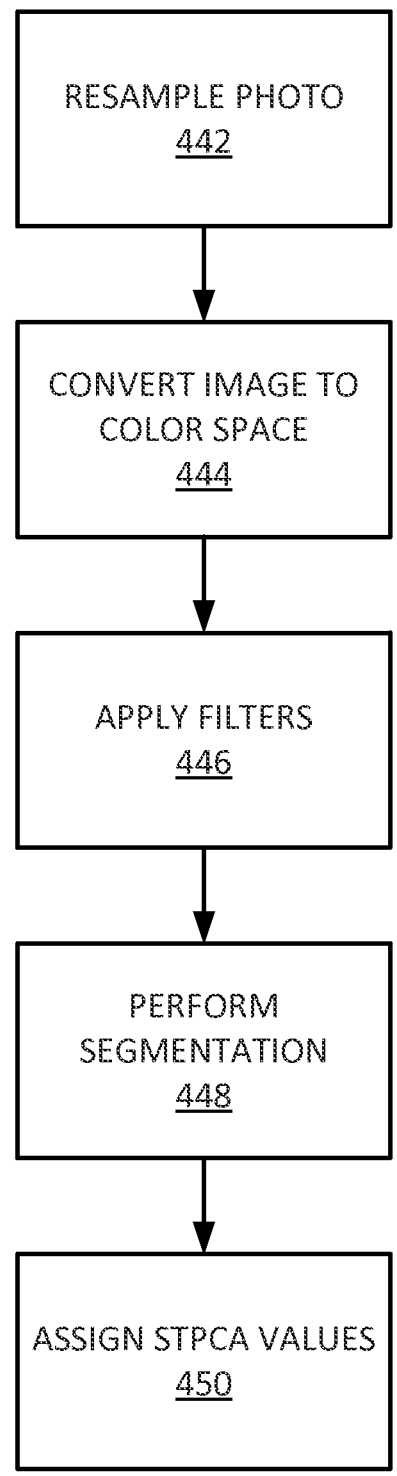

In some implementations, color segmentation is performed as part of the processing of the digital photo. One implementation of a method for performing color segmentation (STEP 440) is shown in FIG. 4C. In STEP 442, the digital photo is resampled to a smaller size that matches the resolution needed for identifying skin tones. The size can be determined by the dimensions of key facial regions; for instance, the size can be calculated as newSampleHeight=(Image.height*128)/sqrt(Area of Face region in Pixels). This resampled photo is referred to hereinafter as the "Segmentation Image."

The Segmentation Image can be converted to a color space using, for example, a 3×3 matrix transform that transforms skin color from an RGB representation to a skin tone principal component representation (STEP 444). The skin tone principal component space will be referred to herein as "STPCA." This transform can be found by performing principal component analysis on an a large array of RGB colors of skin tones from digital photos taken by various Users with matching devices (e.g., a particular mobile phone). This image will be referred to as the "PCA Segmentation Image." Principal component analysis is a well-known method of reducing the dimensionality of a set of vectors.

The principal component channel (channel 0) of the PCA Segmentation Image is prepared for segmentation by applying additional filtering, such as a bandpass filter (STEP 446). In STEP 448, segmentation can be performed by using well-known techniques such as a Watershed transform. The resulting image is referred to herein as the "Segmentation Label Image." The brightest pixel of the PCA Segmentation Image channel 0 within each Segmentation Label image region can then be used to assign an STPCA value to each Segmentation Label Region (STEP 450).

Facial Region Color Assignment

Figure 4D:
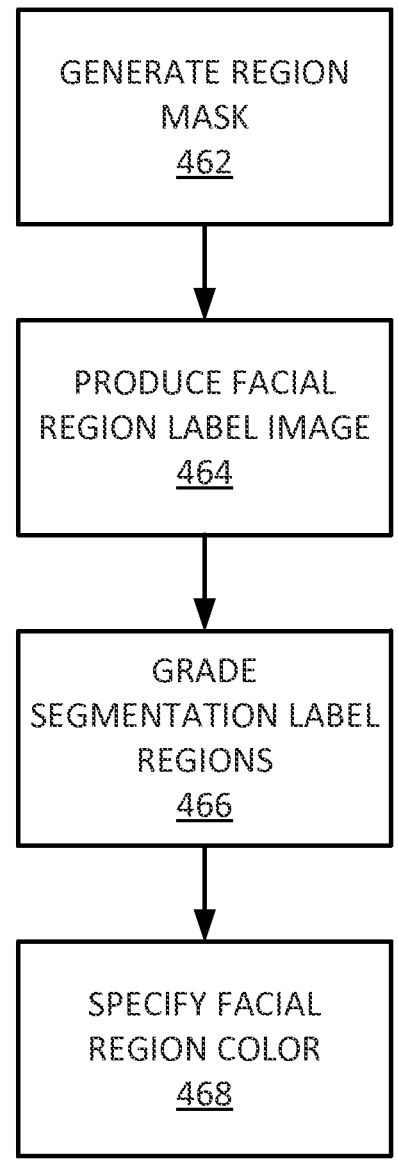

Referring now to FIG. 4D, given the delineation of a facial region, one implementation for determining the skin tone for a region (i.e., STEP 460) is as follows. In STEP 462, a region mask is generated for the facial region by, for example, drawing the region as a white polygon on a black background. The Segmentation Label Image produced by the color segmentation process described above is masked by the region mask to produce a "Facial Region Label Image" (STEP 464). Then, in STEP 466, the Segmentation Label Regions in the Facial Region Label Image are graded by area and by maximizing the distance of the label region's assigned STPCA value from STPCA values representing shadow and specular highlight. The STPCA value for the Segmentation Label Region with the best grade is then specified as the "Facial Region Color" (STEP 468).

Final Facial Region Color Calibration and Additional Data

Figure 4E:
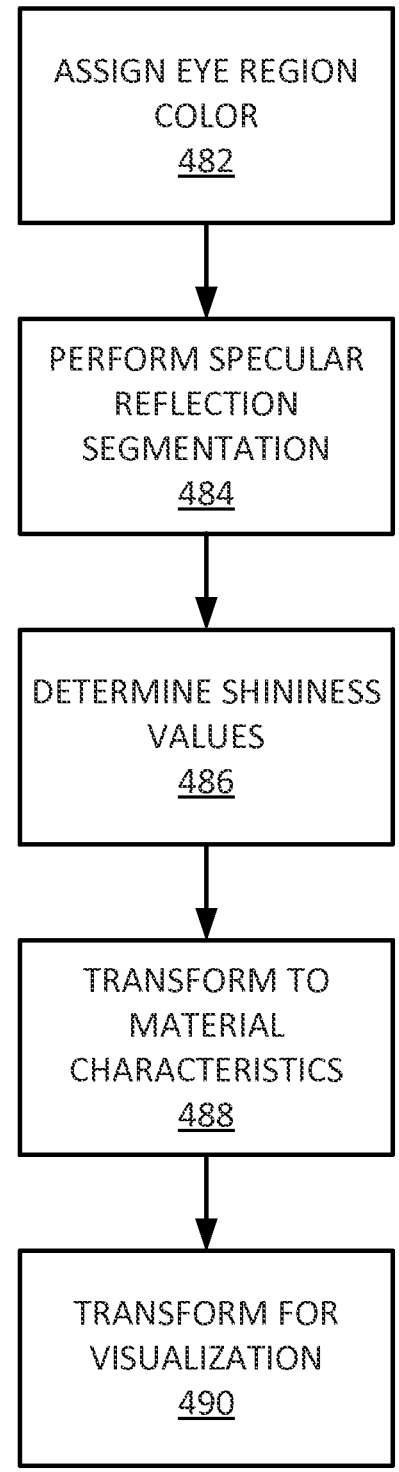

Final facial region color calibration (STEP 480) can be performed using the following steps, as shown in FIG. 4E. In STEP 482, a facial region color for the eyes is determined and assigned and, in particular, a grey level for the sclera of the eye is determined. In STEP 484, segmentation of specular reflection in the eye regions can be used to determine if the flash was fired and if other point sources of light were present (see further description below). Specular reflection sub-regions are detected for each Facial Region, and a "shininess" value is determined for each facial region based on its size relative to the overall region size (STEP 486). The shininess metric for the eyes can also be used to calibrate other regions.

Final transformation of STPCA values, grey level, and shininess values can be transformed directly into material characteristics used for manufacturing of a cosmetic product, rather than an intermediate form (STEP 488). Further, transformation of STPCA into RGB or LAB color spaces can be performed for visualization for the User. These can be performed using a modified version of the original PCA matrix, adjusted by the grey level and shininess value.

As mentioned above, facial region color calibration can involve determining the presence and color of lighting sources (other than known sources, such as a camera flash) based on an evaluation of specular reflection in the eye regions. In one implementation, this process includes the following steps:

1. Subtract the red channel from the digital photograph.
2. Take a bandpass filter of a relatively small number of pixels in the high frequency (e.g., around two pixels), and a higher number of pixels in the low frequency (e.g., around five or six pixels) to remove detail.
3. Perform a histogram on the result and take a threshold at the 99th percent of the pixel population that the histogram has, thereby determining all of the highest lights.
4. Dilate the highest lights by approximately twenty pixels to create a mask for the lights.
5. Apply another bandpass filter to the resulting image at a high frequency of approximately ten pixels and a low frequency of approximately twenty pixels, resulting in an image having broader features, including pulling out the iris of the eye.
6. Dilate the dark part of the eye by approximately ten pixels, resulting in the intersection of the inverse of the iris, or the dark part of the eye, with the discovered highlights.
7. Threshold the bright spots (i.e., reflections of light) within the eye with the initial inputs.
8. Use the resulting spots to mask the original color of the input images and determine if there are previously unknown light sources.
9. Subtract any discovered unknown light sources and color calibrate.

User Data Collection Specific to the Reference Service

The Common Service Data Collection can be augmented by additional data collection which aids the OAPTA Professional Group in the Reference OAPTA Specification. In one implementation, this data includes one or more of:

1. Visible, IR, and UV color spectrographic data.
2. Bidirectional reflectance data.
3. Photomicrographs of specific facial skin sites.
4. Analysis of surface skin oils or residue using a Raman Spectrophotometer, Mass Spectrophotometer, or other instrument.
5. Augmented data provided by the Common Service Data collection by interview.

Reference OAPTA Specification

The OAPTA Professional Group can specify the components and amounts to be used in making a custom OAPTA for a User based on the Reference User Data Collection. The Specification and the Reference User Data can be compiled to create an entry in the OAPTA Metadata 230.

Reference OAPTA Formulation

The OAPTA Professional Group can provide a set of instructions that specify the order and methods that are used to combine the components to make the OAPTA product. This set of instructions can be added to the current entry in the OAPTA Metadata 230.

Reference OAPTA Compounding

In one implementation, the OAPTA product is compounded manually based on the OAPTA Formulation 260. In another implementation, a review of the formulation instructions and the Shared OAPTA Component Set 210 is used to build a device which will automatically compound the OAPTA product based on the formulation instructions.

Reference OAPTA Delivery

In one implementation, the OAPTA product is delivered on premises to the User after being compounded in the same location and during the User's use of the system. In another implementation, the OAPTA product is compounded in another location and shipped to the User.

Reference OAPTA Collection

In one implementation, Collection is accomplished through billing via the Professional Service. In another implementation, payment information is collected as part of the Common Service Data Collection, and payment is collected on OAPTA delivery.

Reference OAPTA Feedback

In one implementation, User feedback is collected through an interview after the OAPTA product is delivered and tested. In another implementation, feedback information is collected by the mobile application used for Common Service Data Collection.

OAPTA Metadata

In one implementation, the OAPTA Metadata 230 include one or more of the following data fields:
1. CommonServiceData
  a. UserID
  b. GeographicRegion
  c. Gender
  d. Birthday
  e. Date
  f. CombinedVector
    i. Ultraviolet Radiation exposure
    ii. Allergy Vector
    iii. nColorVector
2. Reference Specific Data
  a. Skin Color Spectra
  b. Bidirectional Reflectance Data
  c. Photomicrographs of specific facial skin sites
  d. Skin surface oil index
3. Reference Specification
4. Reference Formulation Instructions
5. Tags for spanning trees found in the Specification Hints.

The CombinedVector can be thought of as a point in n-space. The magnitude of each component is normalized to its significance system-wide.

In some implementations, reference data can include one or more ground truth data sets that include defined values relating to, e.g., skin color, reflectance, allergies, and/or other data referenced herein, for which known OAPTAs can be accurately formulated. In other words, for a specific set of values in the ground truth data set, there can be a predefined topical agent that is optimized for those values. The predefined topical agent can also be similar to or the same as an existing product, such as a competitor's commercial offering. Thus, one process for determining an optimal OAPTA for a user can be to determine the relative proximities of the user's captured skin data with the ground truth data set values, and selecting the data set values that are closest in proximity. The OAPTA or existing product corresponding to those closest values can then be the unique compound selected for the user.

OAPTA Production Service

The OAPTA Production Service 240 can be constructed after a sufficient number of records have been collected into the OAPTA Metadata 230, and the Reference Service OAPTA Compounding means have been automated.

Production User Identity

The OAPTA Production Service 240 creates and begins to manage a User identity when a User purchases the mobile application and launches the application for the first time. The Service creates a data store to hold User data, and provides for retrieval of the data based on the User identity. The User identity can also contain shipping and billing information.

Production User Data Collection

The OAPTA Production Service 240 can use the Common Service Data Collection previously described for the OAPTA Reference Service 220. The User's Common Service data for a given session is stored with the Production User identity.

Production OAPTA Specification and Formulation

The OAPTA Production Service 240 uses the OAPTA Metadata 230 generated by the OAPTA Reference Service 220 to synthesize a specification. For example, based on the facial image data gathered and processed as described above, a particular User's complexion can be matched to an existing reference complexion for which a cosmetic formulation has already been defined (e.g., based on an actual reference user, a ground truth data set, etc.). Properties unique to the User, such as allergies, can be considered in determining whether a particular formulation will be compatible with the user. New formulations derived by the system can be saved as references for future use.

In one implementation, to process and order an OAPTA product, the system obtains the User's current Common Service Data that is linked to the User's Production User Identity, and determines the closest match to the Common Service Data combined vector in the OAPTA Metadata 230. If the distance between the combined vector and the closest match is too far, the User can be queried if he or she would like to be promoted to being a reference user and end the current order.

The system can then locate the next closest match filtered by the first match's spanning tree tags, and can use geometric algebra or singular value decomposition to find a third filtered match point describing a hyperplane. If the distance between the combined vector and the surface of the hyperplane is too large, the User can be queried if he or she would like to be promoted to being a reference user and end the current order. For each found reference point, the blend values are determined, and a specification is built by adding blends for each component common to the closest match. Finally, the formulation from the closest match's OAPTA Metadata is selected as the formulation suited to the User.

Production OAPTA Compounding

The system can use the automated compounding method specified by an implementation of the OAPTA Reference Service 220 described herein. In one implementation, this is a shared resource. In another implementation, there are multiple locations with similar automation equipment, and the location closest to the User's geographic location is chosen.

The OAPTA product can be compounded on demand after the User has proceeded through the steps described herein that allow a custom formulation to be determined. Additionally or alternatively, OAPTA products can be compounded in advance (e.g., the most common formulations can be compounded and stocked) to provide for a faster turnaround time from formulation to delivery. In some implementations, the formulation determined by the system is mapped to existing products from other vendors and brands. For instance, based on the formulation, ingredients, color, and/or other known properties of other products, the system can compare the User's formulation with the other products and determine those that are most similar or that meet a threshold of similarity (e.g., 75%, 80%, 90%, and so on). As one example, the system can determine that the User's foundation is an 88% match to an Armani foundation and an 82% match to a L'Oreal foundation. The system can also display the other matched products to the User and allow the User to purchase them in addition to or as an alternative to the User's customized formulation.

Production OAPTA Delivery, Collection, and Feedback

The OAPTA product can be shipped to the User from an automated compounding location, a warehouse, a retail establishment, or other location where OAPTA products can be compounded and/or stored. The User can be billed upon shipment using the Production User identity information available to the system. In one implementation, the User is able to provide feedback and other data using a mobile application which serves the Common Service Data Collection.

OAPTA System Feedback

In one implementation, the OAPTA system 200 is configured to facilitate review of Production OAPTA Feedback 250 and compare any critical feedback to gaps in OAPTA Metadata's 230 Common Service Data combined vector space. The system 200 can adjust the allowable maximum distance from a solution if the space is too sparse, and upgrade Production Users to Reference Users to fill gaps in the model.

Implementations of the OAPTA system 200 can use appropriate hardware or software; for example, the OAPTA system 200 can execute on a system capable of running an operating system such as the Microsoft Windows® operating systems, the Apple OS X® operating systems, the Apple iOS® platform, the Google Android™ platform, the Linux® operating system and other variants of UNIX® operating systems, and the like.

Some or all of the described functionality can be implemented in software and/or hardware on a user device. A user device can include, but is not limited to, a smart phone, smart watch, smart glasses, tablet computer, portable computer, television, gaming device, music player, mobile telephone, laptop, palmtop, smart or dumb terminal, network computer, personal digital assistant, wireless device, information appliance, workstation, minicomputer, mainframe computer, or other computing device, that is operated as a general purpose computer or a special purpose hardware device that can execute the functionality described herein. The software, for example, can be implemented on a general purpose computing device in the form of a computer including a processing unit, a system memory, and a system bus that couples various system components including the system memory to the processing unit.

Additionally or alternatively, some or all of the functionality can be performed remotely, in the cloud, or via software-as-a-service. For example, matching functions can be performed on one or more remote servers or other devices, as described above, that communicate with the user devices. The remote functionality can execute on server class computers that have sufficient memory, data storage, and processing power and that run a server class operating system (e.g., Oracle® Solaris®, GNU/Linux®, and the Microsoft® Windows® family of operating systems).

The systems can include a plurality of software processing modules stored in a memory and executed on a processor. By way of illustration, the program modules can be in the form of one or more suitable programming languages, which are converted to machine language or object code to allow the processor or processors to execute the instructions. The software can be in the form of a standalone application, implemented in a suitable programming language or framework.

Method steps of the techniques described herein can be performed by one or more programmable processors executing one or more computer programs to perform functions by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors. Generally, a processor will receive instructions and data from a read-only memory or a random access memory or both. The essential elements of a computer are a processor for executing instructions and one or more memory devices for storing instructions and data. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. One or more memories can store media assets (e.g., audio, video, graphics, interface elements, and/or other media files), configuration files, and/or instructions that, when executed by a processor, form the modules, engines, and other components described herein and perform the functionality associated with the components. The processor and the memory can be supplemented by, or incorporated in special purpose logic circuitry.

In various implementations, a user device includes a web browser, native application, or both, that facilitates execution of the functionality described herein. A web browser allows the device to request a web page or other downloadable program, applet, or document (e.g., from the server(s)) with a web page request. One example of a web page is a data file that includes computer executable or interpretable information, graphics, sound, text, and/or video, that can be displayed, executed, played, processed, streamed, and/or stored and that can contain links, or pointers, to other web pages. In one implementation, a user of the device manually requests a web page from the server. Alternatively, the device automatically makes requests with the web browser. Examples of commercially available web browser software include Microsoft® Internet Explorer®, Mozilla®, Firefox®, and Apple®, Safari®.

In some implementations, the user devices include client software. The client software provides functionality to the device that provides for the implementation and execution of the features described herein. The client software can be implemented in various forms, for example, it can be in the form of a native application, web page, widget, and/or Java, JavaScript, .Net, Silverlight, Flash, and/or other applet or plug-in that is downloaded to the device and runs in conjunction with the web browser. The client software and the web browser can be part of a single client-server interface; for example, the client software can be implemented as a plug-in to the web browser or to another framework or operating system. Other suitable client software architecture, including but not limited to widget frameworks and applet technology can also be employed with the client software.

A communications network can connect the devices with one or more servers and/or with each other. The communication can take place over media such as standard telephone lines, LAN or WAN links (e.g., T1, T3, 56 kb, X.25), broadband connections (ISDN, Frame Relay, ATM), wireless links (802.11 (Wi-Fi), Bluetooth, GSM, CDMA, etc.), for example. Other communication media are possible. The network can carry TCP/IP protocol communications, and HTTP/HTTPS requests made by a web browser, and the connection between the clients and servers can be communicated over such TCP/IP networks. Other communication protocols are possible.

The system can also be practiced in distributed computing environments where tasks are performed by remote processing devices that are linked through a communications network. In a distributed computing environment, program modules can be located in both local and remote computer storage media including memory storage devices. Other types of system hardware and software than that described herein can also be used, depending on the capacity of the device and the amount of required data processing capability. The system can also be implemented on one or more virtual machines executing virtualized operating systems such as those mentioned above, and that operate on one or more computers having hardware such as that described herein.

In some cases, relational or other structured databases can provide such functionality, for example, as a database management system which stores data for processing. Examples of databases include the MySQL Database Server or ORACLE Database Server offered by ORACLE Corp. of Redwood Shores, Calif., the PostgreSQL Database Server by the PostgreSQL Global Development Group of Berkeley, Calif., or the DB2 Database Server offered by IBM.

It should also be noted that implementations of the systems and methods can be provided as one or more computer-readable programs embodied on or in one or more articles of manufacture. The program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

Certain implementations of the present invention were described above. It is, however, expressly noted that the present invention is not limited to those implementations, but rather the intention is that additions and modifications to what was expressly described herein are also included within the scope of the invention. Moreover, it is to be understood that the features of the various implementations described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of determining a customized cosmetic formulation, the method comprising:
    interactively guiding a user through capture of one or more images using a device having an image sensor, each image comprising a skin region of the user;
    processing the skin region images to provide calibrated skin color information, the processing comprising:
        identifying a plurality of specific facial regions of the user in one or more of the skin region images;
        determining a skin tone of each specific facial region;
        segmenting the specific facial regions based on skin tone;
        assigning a color to each specific facial region segment based on at least one of skin tone, shadow, and specular highlight; and
        determining the calibrated skin color information based at least in part on the determined skin tone of each specific facial region;
    comparing the calibrated skin color information to a ground truth data set to identify a set of closest known values in the ground truth data set, wherein the ground truth data set comprises a plurality of sets of skin data values, each set of skin data values associated with a predefined cosmetic formulation; and
    automatically determining a customized cosmetic formulation for the user based on the comparison, wherein the customized cosmetic formulation comprises at least one of:
        (i) a unique compound that is derived based on a relative proximity of the calibrated skin color information to the set of closest known values; and
        (ii) an existing cosmetic product.

2. The method of claim 1, further comprising receiving ambient lighting information associated with at least one of the skin region images, and wherein the at least one skin region image is processed based at least in part on the ambient lighting information.

3. The method of claim 1, further comprising interactively guiding the user through capture of an image of a marker using the device image sensor, wherein the skin region images are processed based at least in part on the marker image.

4. The method of claim 3, further comprising storing current settings of the device image sensor based on a successful capture of the marker image.

5. The method of claim 4, wherein the device image sensor settings comprise at least one of exposure, focus, and white balance.

6. The method of claim 4, wherein the skin region images are processed based on the stored image sensor settings.

7. The method of claim 1, wherein processing the skin region images comprises:
    identifying one or more unknown light sources based on specular reflection in an eye region of the user; and
    compensating for the one or more unknown light sources.

8. The method of claim 1, wherein the skin region is selected from the group consisting of a wrist, a forehead, a left cheek, a right cheek, and a full face.

9. The method of claim 1, further comprising allowing the user to purchase the existing cosmetic product.

10. The method of claim 1, wherein the device is selected from the group consisting of a mobile phone, a tablet, a digital camera, a webcam, smart glasses, a television, and a gaming console.

11. A system for determining a customized cosmetic formulation, the system comprising:
    at least one computer comprising a memory for storing computer-executable instructions and a processing unit for executing the instructions stored in the memory, wherein the execution of the instructions configures the computer to perform operations comprising:
        interactively guiding a user through capture of one or more images using a device having an image sensor, each image comprising a skin region of the user;
        processing the skin region images to provide calibrated skin color information, the processing comprising:

identifying a plurality of specific facial regions of the user in one or more of the skin region images;
determining a skin tone of each specific facial region;
segmenting the specific facial regions based on skin tone;
assigning a color to each specific facial region segment based on at least one of skin tone, shadow, and specular highlight; and
determining the calibrated skin color information based at least in part on the determined skin tone of each specific facial region;
comparing the calibrated skin color information to a ground truth data set to identify a set of closest known values in the ground truth data set, wherein the ground truth data set comprises a plurality of sets of skin data values, each set of skin data values associated with a predefined cosmetic formulation; and
automatically determining a customized cosmetic formulation for the user based on the comparison, wherein the customized cosmetic formulation comprises at least one of:
(i) a unique compound that is derived based on a relative proximity of the calibrated skin color information to the set of closest known values; and
(ii) an existing cosmetic product.

12. The system of claim 11, wherein the operations further comprise receiving ambient lighting information associated with at least one of the skin region images, and further wherein the at least one skin region image is processed based at least in part on the ambient lighting information.

13. The system of claim 11, wherein the operations further comprise interactively guiding the user through capture of an image of a marker using the device image sensor, wherein the skin region images are processed based at least in part on the marker image.

14. The system of claim 13, wherein the operations further comprise storing current settings of the device image sensor based on a successful capture of the marker image.

15. The system of claim 14, wherein the device image sensor settings comprise at least one of exposure, focus, and white balance.

16. The system of claim 14, wherein the skin region images are processed based on the stored image sensor settings.

17. The system of claim 11, wherein processing the skin region images comprises:
identifying one or more unknown light sources based on specular reflection in an eye region of the user; and
compensating for the one or more unknown light sources.

18. The system of claim 11, wherein the skin region is selected from the group consisting of a wrist, a forehead, a left cheek, a right cheek, and a full face.

19. The system of claim 11, wherein the operations further comprise allowing the user to purchase the existing cosmetic product.

20. The system of claim 11, wherein the device is selected from the group consisting of a mobile phone, a tablet, a digital camera, a webcam, smart glasses, a television, and a gaming console.

* * * * *